United States Patent [19]

Tsoi

[11] Patent Number: 4,978,605
[45] Date of Patent: Dec. 18, 1990

[54] BENZOYLACETANILIDE PHOTOGRAPHIC YELLOW DYE IMAGE-FORMING COUPLERS AND PHOTOGRAPHIC ELEMENTS CONTAINING THEM

[75] Inventor: Siu C. Tsoi, Watford, United Kingdom

[73] Assignee: Eastman Kodak Company, Rochester, N.Y.

[21] Appl. No.: 295,081

[22] Filed: Jan. 6, 1989

[30] Foreign Application Priority Data

Feb. 1, 1988 [GB] United Kingdom ............... 8802129

[51] Int. Cl.$^5$ .............................................. G03C 7/36
[52] U.S. Cl. ...................................... 430/557; 430/389
[58] Field of Search ..................... 430/557, 556, 389

[56] References Cited

U.S. PATENT DOCUMENTS

| | | | |
|---|---|---|---|
| 3,725,072 | 4/1973 | Yoshida et al. | 430/389 |
| 4,230,851 | 10/1980 | Renner et al. | 430/556 |
| 4,266,019 | 5/1981 | Kobayashi et al. | 430/551 |
| 4,326,024 | 4/1982 | Kobayashi et al. | 430/557 |
| 4,327,175 | 4/1982 | Toda et al. | 430/557 |
| 4,476,219 | 10/1984 | Sakanoue et al. | 430/557 |
| 4,511,649 | 4/1985 | Ogawa et al. | 430/557 |
| 4,529,691 | 7/1985 | Renner et al. | 430/556 |
| 4,587,207 | 5/1986 | Tsada et al. | 430/557 |
| 4,710,453 | 12/1987 | Hirabayashi et al. | 430/557 |
| 4,758,501 | 7/1988 | Buckland et al. | 430/557 |
| 4,783,397 | 11/1988 | Ogawa et al. | 430/557 |
| 4,824,773 | 4/1989 | Sato et al. | 430/557 |

OTHER PUBLICATIONS

*Research Disclosure,* Dec. 1978, Item #17643 Kenneth Mason Publications Ltd.

*Primary Examiner*—Richard L. Schilling
*Attorney, Agent, or Firm*—Richard E. Knapp

[57] ABSTRACT

A non-diffusible, yellow dye image-forming benzoylacetanilide coupler having an aryloxy coupling-off group where (a) the benzoyl group comprises a substituent $R^1O—$ wherein $R^1$ is an alicyclic or aliphatic, unsubstituted or substituted, branched or unbranched hydrocarbon group; and, (b) at least one of the benzoyl group and acetanilide group comprise a substituent that comprises a branched alkyl group containing at least 4 carbon atoms wherein the alkyl chains are uninterrupted or interrupted by hetero atoms or groups, enables improved solubility in coupler solvents in a photographic material, and the yellow dyes resulting from such couplers upon oxidative coupling have improved light stability. Such couplers are advantageous in photographic silver halide elements and processes.

11 Claims, No Drawings

BENZOYLACETANILIDE PHOTOGRAPHIC YELLOW DYE IMAGE-FORMING COUPLERS AND PHOTOGRAPHIC ELEMENTS CONTAINING THEM

This invention relates to benzoylacetanilide photographic yellow dye image forming couplers and to photographic elements containing them.

2-Equivalent couplers of the benzoylacetanilide class are known which contain a heterocyclic coupling-off group, for example as described in U.S. Pat. Nos. 4,230,851, 4,327,175 and 4,529,691. Such couplers have good solubility in conventional coupler solvents.

These same U.S. Patents also describe couplers in a related class, the pivaloylacetanilides. These couplers again have good solubility in conventional coupler solvents regardless of the nature of the coupling-off group.

Fortuitously, some of the couplers generally referred to in the above U.S. patents contain branched alkyl groups but no data are given to establish whether such couplers have any particular properties which their unbranched analogues do not.

Recently, benzoylacetanilide couplers having aryloxy coupling-off groups have been of interest as providing image dyes of excellent hue and high extinction coefficient. These couplers, however, do tend to be less soluble in coupler solvents than is desirable.

The present invention provides couplers of this class having improved solubility in coupler solvents by virtue of a branched alkyl group having more than three carbon atoms in the benzoyl and/or anilide moiety compared to their straight chain or iso-propyl analogues. Additionally the image dyes formed therefrom have improved light stability.

This invention provides new non diffusible, yellow dye, image forming benzoylacetanilide couplers having aryloxy coupling-off groups that are advantageous in photographic materials. In these new couplers (a) the benzoyl group comprises a substituent $R^1O$— wherein $R^1$ is an alicyclic or aliphatic, unsubstituted or substituted, branched or unbranched hydrocarbon group; and, (b) at least one of the benzoyl group and the acetanilide group comprise a substituent that comprises a branched alkyl group containing at least 4 carbon atoms wherein the alkyl chains are uninterrupted or interrupted by hetero atoms or groups. In a photographic element, particularly a color photographic silver halide element, comprising a support bearing at least one photographic silver halide emulsion layer, such new couplers enable improved solubility in coupler solvents and the dyes resulting from such couplers upon oxidative coupling have improved light stability.

The described benzoylacetanilide couplers are typically represented by the formula:

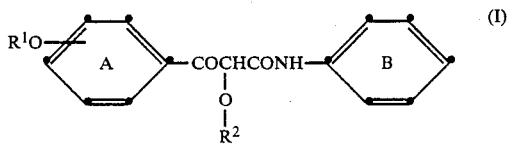

(I)

wherein
$R^1$ is an alicyclic or aliphatic hydrocarbon group which may be substituted or unsubstituted, branched or unbranched, $R^2$ is an aryl group which may be substituted or unsubstituted, and wherein at least one of the rings A and B contains a substituent (which may be $R^1$) comprising a branched alkyl group having at least 4 carbon atoms wherein the alkyl chains are optionally interrupted by hetero atoms or groups. The branched alkyl group preferably has 4 to 30 carbon atoms, such as 4 to 15 carbon atoms.

In one embodiment of the invention the branched alkyl group contains at least one chiral carbon atom, i.e. a carbon atom which is attached to four different atoms or groups. The presence of such chiral carbon atoms enables the compound to exist as stereo-isomers. If the branched alkyl group contains 4 or 5 carbon atoms, the influence of a chiral center is particularly significant. For example sec-butyl is preferable to t-butyl.

Examples of the groups which $R^1$ may represent are alicyclic groups of 5 to 6 carbon atoms, and non cyclic groups of 1–20 carbon atoms which may be substituted or unsubstituted, saturated or unsaturated, e.g. methyl, ethyl, n-butyl, n-dodecyl, n-hexadecyl, and n-undecyl. If $R^1$ comprises a branched alkyl group as specified above, examples include

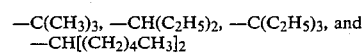

(which do not contain a chiral carbon atom) and

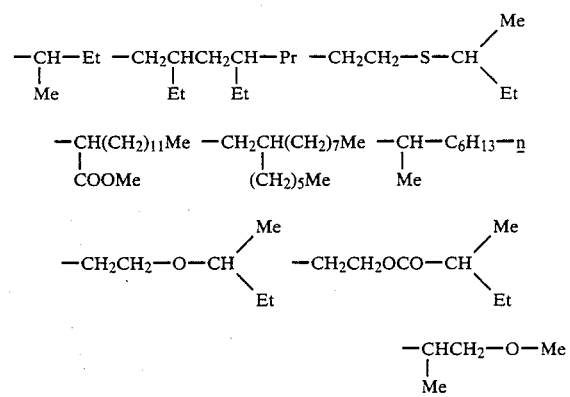

(which do contain one or more chiral carbon atoms). In this specification Me stands for methyl, Et for ethyl, Pr for propyl and Bu for butyl.

The present couplers are non diffusible in photographic elements hence will contain one or more ballasting substituents of sufficient size and configuration to ensure this. The necessary bulk may be divided among more than one substituent if desired. The ballast groups may form part of $R^1$ and/or may be directly or indirectly linked to one or both of rings (A) and (B). Such groups may comprise any of the branched alkyl groups listed above in connection with the group $R^1$.

When a branched alkyl group is attached to ring (B) it is preferably via a linking group which may, for example, be —CO—O—, —O—CO—, —O—, —S—,

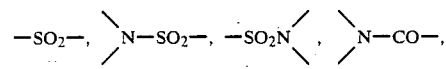

-continued

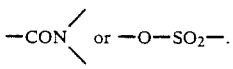

The aryl group $R^2$ may be substituted with one or more substituents selected from alkyl, amide, ester, ketone, carbamoyl, sulphonamide, sulphamoyl, sulphone, ether, thioether, nitrile, nitro groups and halogen atoms in any position.

A preferred group of couplers according to the present invention have the general formula:

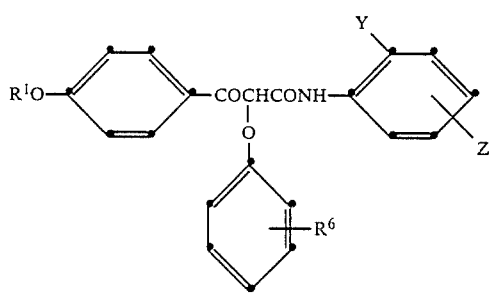

wherein
$R^1$ is an alicyclic or aliphatic hydrocarbon group which may be substituted or unsubstituted, branched or unbranched and may comprise a ballast group,
Y is chloro or trifluoromethyl,
Z is —L—$R^5$, —$SO_2NR^3R^4$, halogen or trifluoromethyl, where $R^5$ is an aliphatic hydrocarbon group which may be substituted or unsubstituted, branched or unbranched, $R^3$ and $R^4$ are each hydrogen or an aliphatic hydrocarbon group which may be substituted or unsubstituted, branched or unbranched or $R^3$ and $R^4$ together form a ring, $R^6$ is one or more substituents selected from alkyl, amide, ester, ketone, carbamoyl, sulphonamide, sulphamoyl, sulphone, ether, thioether, nitrile, nitro groups and halogen atoms, L is a direct bond or a carbamoyl (—CONH—), amido (—NHCO—), oxycarbonyl (—CO—O—), carbonyloxy (—O—CO—), sulphonate (—O—$SO_2$—), ether (—O—), sulphamoyl

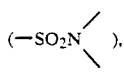

sulphonamide

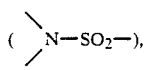

phosphate (—O—$PO_3$—) or alkylene group;
wherein at least one of Z and $R^1$ comprises a branched alkyl group having at least 4 carbon atoms, and containing alkyl chains that may be interrupted by hetero atoms or groups; and wherein the coupler contains one or more ballast groups of sufficient size and configuration to render it non-diffusible in photographic layers.

Examples of coupling-off groups ($R^2O$— in formula (I)) are shown below together with the names by which they will be identified herein:

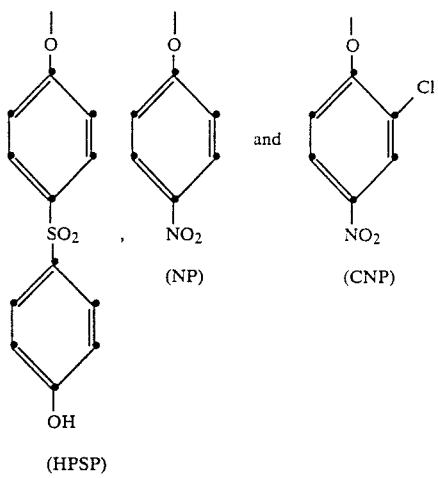

The dye forming couplers of this invention can be used in the ways and for the purposes that dye-forming couplers have been previously used in the photographic art.

Typically, the couplers are associated with silver halide emulsion layer coated on a support to form a photographic element. As used herein, the term "associated with" signifies that the coupler is incorporated in the silver halide emulsion layer or in a layer adjacent thereto where, during processing, it is capable of reacting with silver halide development products.

Typically the coupler is dissolved in a coupler solvent and this solution is dispersed in an aqueous gelatin solution. Examples of coupler solvents that may be used are dibutyl phthalate, tricresyl phosphate, diethyl lauramide and 2,4-di-tertiary-amylphenol. In addition an auxiliary coupler solvent may also be used, for example ethyl acetate, cyclohexanone, and 2-(2-butoxy-ethoxy)ethyl acetate, which are removed from the dispersion before incorporation into the photographic material.

The photographic elements can be single color elements or multicolor elements. In a multicolor element, the yellow dye-forming couplers of this invention would usually be associated with a blue-sensitive emulsion, although they could be associated with an emulsion sensitized to a different region of the spectrum, or with a panchromatically sensitized, orthochromatically sensitized or unsensitized emulsion. Multicolor elements contain dye image-forming units sensitive to each of the three primary regions of the spectrum. Each unit can be comprised of a single emulsion layer or of multiple emulsion layers sensitive to a given region of the spectrum. The layers of the elements, including the layers of the image-forming units, can be arranged in various orders as known in the art.

A typical multicolor photographic element comprises a support bearing a yellow dye image-forming unit comprised of at least one blue-sensitive silver halide emulsion layer having associated therewith at least one yellow dye-forming coupler being a coupler of this invention, and magenta and cyan dye image-forming units comprising at least one green- or red-sensitive silver halide emulsion layer having associated therewith at least one magenta or cyan dye-forming coupler respectively. The element can contain additional layers, such as filter layers.

In the following discussion of suitable materials for use in the emulsions and elements of this invention, reference will be made to Research Disclosure, December 1978, Item 17643, published by Industrial Opportunities Ltd., The Old Harbourmaster's, 8 North Street, Emsworth, Hants PO10 7DD, U.K. This publication will be identified hereafter as "Research Disclosure".

The silver halide emulsion employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein. The couplers of this invention and any additional couplers can be incorporated in the elements and emulsions as described in Research Disclosures of Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section X), coating aids (see Research Disclosure Section XI), plasticizers and lubricants (see Research Disclosure Section XII), matting agents (see Research Disclosure Section XVI) and development modifiers (see Research Disclosure Section XXI).

The photographic elements can be coated on a variety of supports as described in Research Disclosure Section XVII and the references described therein.

The photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the elements with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-$\beta$-(methylanesulphonamido)-(ethylaniline sulphate hydrate, 4-amino-3-methyl-N-ethyl-N-$\beta$-(methanesulphonamido)ethyl-N,N-diethylaniline hydrochloride and 4-amino-N-ethyl-N-(2-methoxy-ethyl)-m-toluidine di-p-toluene sulphonate.

With negative-working silver halide emulsions this processing step leads to a negative image. To obtain a positive (or reversal) image, this step can be preceded by development with a non-chromagenic developing agent to develop exposed silver halide, but not form dye, and then uniform fogging of the elements to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Specific examples of couplers according to the present invention are listed in Table I below.

TABLE I

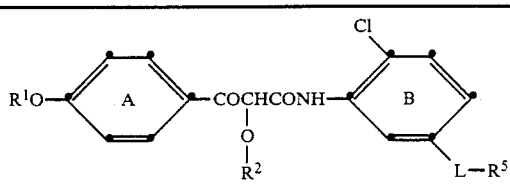

| Coupler | $R^1$ | L | $R^5$ | $-OR^2$ |
|---|---|---|---|---|
| A1 | Me(CH$_2$)$_{11}$CH—<br>\|<br>CO$_2$Me | — | Cl | (HPSP) |
| A2 | n-Bu | CO$_2$ | —CH(CH$_2$)$_4$Me<br>\|<br>(CH$_2$)$_4$Me | " |
| A3 | " | " | —CH$_2$CHCH$_2$CHPr<br>\|   \|<br>Et  Et | " |
| A4 | EtCH—<br>\|<br>Me | " | —C$_{12}$H$_{25}$-n | " |
| A5 | n-C$_6$H$_{13}$— | " | —CH$_2$CHCH$_2$CHPr<br>\|   \|<br>Et  Et | " |
| A6 | n-Bu | " | " | (NP) |

TABLE I-continued

[Structure: R¹O—(A)—COCHCONH—(B), with R² on O below the CH, Cl on ring B, and L—R⁵ on ring B]

| Coupler | R¹ | L | R⁵ | —OR² |
|---|---|---|---|---|
| A7 | PrCHCH₂CHCH₂— (with Et, Et substituents) | — | CF₃ | (CNP) |
| A8 | " | CO₂ | Me | " |
| A9 | Me | " | —CH₂CH(CH₂)₇Me, (CH₂)₅Me | (HPSP) |
| A10 | Me | " | —CH₂CHCH₂CHPr (Et, Et) | " |
| A11 | Me | CO₂ | —CH₂CHCH₂CHPr (Et, Et) | (CNP) |
| A12 | Me | CO₂ | —CH₂CHCH₂CHPr (Et, Et) | (NP) |
| A13 | Me | O | —CH₂CH(CH₂)₇Me, (CH₂)₅Me | (HPSP) |
| A14 | Me | O | —CH₂CHCH₂CHPr (Et, Et) | " |
| A15 | Me(CH₂)₇CHCH₂— (CH₂)₅Me | O | Me | " |
| A16 | Me(CH₂)₅CH— Me | CO₂ | —C₁₂H₂₅-n | " |

The present couplers may be prepared by methods in themselves known. A specific preparative example is given below.

Preparation of coupler A6

(a) 2,4-diethylheptan-1-yl 4-chloro-3-nitrobenzoate

A mixture of 4-chloro-3-nitrobenzoic acid (60.5g, 0.3 mol), 2,4-diethylheptan-1-ol (51.6g, 0.3 mol) and p-toluenesulphonic acid monohydrate (0.5g) in toluene (600 cm³) was heated to reflux under Dean and Stark condition for 24 hours. After cooling to room temperature, the reaction mixture was washed with sodium hydroxide solution (3M, 200cm³) followed by brine (2×300 cm³). After drying over MgSO₄, the solvent was evaporated off under reduced pressure to give a brown oil. The crude product was dissolved in a 1:4 mixture of ethyl acetate and petroleum ether (boiling point 60°-80° C.) and filtered through a pad of silica gel. The filtrate was evaporated under reduced pressure to give a brown oil (105.2g, 99%) which was used in the next reaction without further purification.

(b) 2,4-diethylheptan-1-yl 3-amino-4-chlorobenzoate

Iron metal powder (82.4g, 1.48mol) was added portionwise, over a period of 10 minutes, to a solution of the nitro compound (105g, 0.295mol) from (a) in acetic acid (560cm³) and water (56cm³), heated on a steam bath. Heating was continued for a further one hour, after which the suspension was filtered hot through kieselguhr. The filtrate was poured into a mixture of ice/water (1.5l) and extracted with ethyl acetate (4×400cm³). The combined extracts were washed with water (1l) and dried over MgSO₄. The solvent was then removed by evaporation under reduced pressure to give the product (89g, 92%) as a brown oil which was used in the next reaction without purification.

(c) 2.4-Diethylheptan-1-yl 3-[3-(4-butoxyphenyl)-3-oxopropanamidon]-4-chloro-benzoate A solution of the aniline from (b) (45g, 138.3mmol) and ethyl 3-(4-butoxyphenyl)-3-oxopropanoate (36.4g, 138mmol) in xylene (500cm³) were heated under reflux, using a Dean and Stark apparatus, for 5 hours. Over the final hour, the volume of the mixture was reduced to 200cm³ by distillation. Petroleum ether (boiling point 60–80° C.) (1 liter) was added with cooling and the solid collected by filtration. The product was isolated as a white solid (44g, 59%).

Found : C, 68.3; H, 8.0; Cl, 6.3; N, 2.7 C₃₁H₄₂ClNO₅: C, 68.4; H, 7.8; Cl, 6.5; N, 2.6%

(d) 2,4-Diethylheptan-1-yl 3-[3-(4-butoxyphenyl)-2-chloro-3-oxopropanamido]-4-chlorobenzoate Sulphuryl chloride (10.85g, 80.4mmol) in dichloromethane (20cm³) was slowly added to a solution of the 4 equivalent coupler from (c) (43.75g, 80.4mmol) in dichloromethane (600cm³). After stirring at room temperature for 20 hours, the volatiles were removed by evaporation under reduced pressure. The product was isolated as a yellow syrup (48g, 99%) and was used in the next reaction without further purification.

(e) 2,4-Diethylheptan-1-yl 3-[3-(4-butoxyphenyl)-2-(4-nitrophenoxy)-3-oxopropanamido]-4-chlorobenzoate. Coupler A6

Triethylamine (10.1g, 100mmol) was added to a solution of the chloro coupler from (d) (24g, 41.5 mmol) and 4-nitrophenol (17.3g, 124.5 mmol) in dry dimethyl formamide (90cm³) at 45°–50° C. which has been degassed with nitrogen. After stirring at 45°–50° C. under nitrogen for 3 hours, the mixture was cooled and poured slowly into cold water (1000cm³) and conc. hydrochloric acid (10cm³), with rapid stirring. Ethyl acetate (100cm³), was then added and after stirring for 5 minutes a yellow solid separated. The solid was collected by filtration and recrystallized from ethanol to give the product as a white solid (13g, 46%).

Found : C, 65.1; H, 6.6; Cl, 5.0; N, 4.1
$C_{31}H_{42}ClNO_5$: C, 65.2; H, 6.6; Cl, 5.2; N, 4.1%

The following couplers of this invention were prepared in a similar manner to coupler A6 from the appropriate starting materials. Table II summarizes their elemental analyses.

TABLE II

| Couplers | Found | | | | | | Requires | | | | | |
|---|---|---|---|---|---|---|---|---|---|---|---|---|
| | C | H | Cl | F | N | S | C | H | Cl | F | N | S |
| A1 | 62.2 | 5.9 | 8.8 | — | 1.7 | 4.1 | 62.1 | 5.8 | 8.7 | — | 1.7 | 4.0 |
| A2 | 64.4 | 6.2 | 4.3 | — | 1.8 | 4.0 | 65.2 | 6.3 | 4.5 | — | 1.8 | 4.0 |
| A3 | 65.5 | 6.5 | 4.4 | — | 1.8 | 3.9 | 65.2 | 6.4 | 4.5 | — | 1.8 | 4.1 |
| A4 | 65.2 | 6.3 | 4.3 | — | 1.6 | 3.9 | 65.5 | 6.5 | 4.4 | — | 1.7 | 4.0 |
| A5 | 65.7 | 6.6 | 4.2 | — | 1.7 | 3.8 | 65.9 | 6.6 | 4.3 | — | 1.7 | 3.9 |
| A7 | 58.6 | 5.6 | 9.5 | 8.1 | 3.9 | — | 58.0 | 5.1 | 10.4 | 8.3 | 4.1 | — |
| A8 | 60.5 | 5.8 | 10.5 | — | 4.0 | — | 60.6 | 5.7 | 10.5 | — | 4.2 | — |
| A9 | 65.5 | 6.6 | 4.2 | — | 1.7 | 4.2 | 65.9 | 6.6 | 4.3 | — | 1.7 | 3.9 |
| A10 | 63.7 | 6.2 | 4.6 | — | 1.7 | 4.2 | 65.9 | 6.6 | 4.3 | — | 1.9 | 4.3 |
| A12 | 64.2 | 6.2 | 5.3 | — | 4.5 | — | 63.9 | 6.1 | 5.6 | — | 4.4 | — |
| A13 | 66.7 | 6.9 | 4.6 | — | 1.8 | 4.3 | 66.7 | 6.9 | 4.5 | — | 1.8 | 4.1 |
| A14 | 64.6 | 6.1 | 4.9 | — | 1.9 | 4.7 | 64.9 | 6.1 | 4.9 | — | 1.9 | 4.4 |
| A15 | 66.8 | 6.8 | 4.5 | — | 1.7 | 4.3 | 66.7 | 6.9 | 4.5 | — | 1.8 | 4.1 |
| A16 | 66.8 | 7.1 | 4.3 | — | 1.4 | 3.5 | 66.9 | 7.0 | 4.1 | — | 1.6 | 3.7 |

The following Table III lists comparative couplers containing straight chain or isopropyl alkyl groups. The group —OR₂ is, in every case, identical to that on the comparable A coupler of Table I.

TABLE III

| Coupler (comparison) | $R^1$ | L | $R^5$ |
|---|---|---|---|
| B1 (A1) | n-$C_{12}H_{25}$— | — | Cl |
| B2 (A2–A4) | n-Bu— | $CO_2$ | —$C_{12}H_{25}$-n |
| B5 (A5,A16) | n-$C_6H_{13}$— | " | —$C_{12}H_{25}$-n |
| B6 (A6) | n-Bu | " | —$C_{12}H_{25}$-n |
| B7 (A7) | n-$C_{12}H_{25}$— | — | $CF_3$ |
| B8 (A8) | n-$C_{12}H_{25}$— | $CO_2$ | Me |
| B9 (A9) | Me | $CO_2$ | —$C_{16}H_{33}$-n |
| B10 (A10) | Me | $CO_2$ | —$C_{12}H_{25}$-n |
| B11 (A11) | Me | $CO_2$ | —$C_{12}H_{25}$-n |
| B12 (A12) | Me | $CO_2$ | —$C_{12}H_{25}$-n |

TABLE III-continued

| Coupler (comparison) | $R^1$ | L | $R^5$ |
|---|---|---|---|
| B13 (A13) | Me | O | —$C_{16}H_{33}$-n |
| B14 (A14) | Me | O | —$C_{12}H_{25}$-n |
| B15 (A15) | n-$C_{16}H_{33}$— | O | Me |

The following Examples are included for a better understanding of the invention.

EXAMPLE 1

Solubility Test for Couplers

Each test coupler (0.24g) together with di-n-butylphthalate (0.12g) and ethyl acetate (0.72g) was accurately weighed into a standard test tube with a plug of cotton wool at the top. The samples were placed in a preheated water bath at 75°–80° C., with occasional agitation, for 15 minutes and then allowed to stand at room temperature. The samples were examined for crystallization (or sign of opacity) at the following time intervals: 5, 10, 15, 20, 25, 30, 45, 60, 90 and 120 minutes after being removed from the water bath.

The results are given in Table IV together with those of comparative couplers of the prior art (couplers of Table III). It can be seen that the couplers of the present invention exhibit superior solubility over their straight chain counterparts.

The test is considered to be a good indication of how a coupler solvent will behave in a photographic coating. A better indicator is, however, the examination of an actual coating as described in Example 3 below.

TABLE IV

| Coupler | Time remained as clear Solution/min. |
|---|---|
| A1 | >120 |
| B1 | 15 |
| A2 | >120 |
| A3 | >120 |
| A4 | 30 |
| B2 | 5 |
| A5 | >120 |
| A16 | >120 |
| B5 | 5 |
| A6 | 60 |
| B6 | <5 |
| A7 | >120 |
| B7 | 5 |
| A8 | 60 |
| B8 | <5 |

TABLE IV-continued

| Coupler | Time remained as clear Solution/min. |
|---------|--------------------------------------|
| A9      | >120                                 |
| B9      | 45                                   |
| A10     | >120                                 |
| B10     | 120                                  |
| A11     | >120                                 |
| B11     | 90                                   |
| A12     | >120                                 |
| B12     | 60                                   |
| A13     | >120                                 |
| B13     | 120                                  |
| A14     | >120                                 |
| B14     | 20                                   |
| A15     | >120                                 |
| B15     | 30                                   |

Comparative solubility tests were carried out for couplers containing short alkyl groups (outside the scope of the present invention) using the same method. The results are shown below in Table V.

TABLE V

RO—⟨⟩—COCHCONH—⟨⟩—Cl, COOC$_{12}$H$_{25}$-n
(—OR$_2$ = HPSP) R$_2$
|
O

| Coupler | R         | Time remained as clear solution/min. |
|---------|-----------|--------------------------------------|
| B16     | iso-propyl| 5                                    |
| B10     | methyl    | 120                                  |
| B17     | ethyl     | 5                                    |
| B2      | n-butyl   | 5                                    |

It can be seen that the branched group, iso-propyl does not show any sign of increasing the solubility of the coupler or the light stability of the dye (see Table VI).

EXAMPLE 2

Dye Image Light Stability

Coupler A9 of Table I was dissolved in half its weight of di-n-butylphthalate, with one and a half times its weight of cyclohexanone as auxiliary solvent and dispersed in gelatin. The auxiliary solvent was removed from the dispersion by continuous washing for 6 hours at 4° C. and pH 6.0.

Photographic coatings were prepared by coating a cellulose acetate film support with a photosensitive layer comprising a dispersion of the novel coupler as formulated above coated at a laydown of 1.93 mmol/m$^2$, a silver bromoiodide emulsion at 0.81g Ag/m$^2$ and gelatin at 2.42 g/m$^2$. An overcoat containing gelatin at 0.89 g/m$^2$ was applied to the photosensitive layer. Bis-vinyl sulphonylmethane at 1.75% by weight of the total gelatin in the pack was also incorporated into the photosensitive layer. The coatings were then slit and chopped into 35 mm × 12 inch strips.

An internal reference coupler for each of the coating sets was used in order to normalize results from different sets. It has the formula:

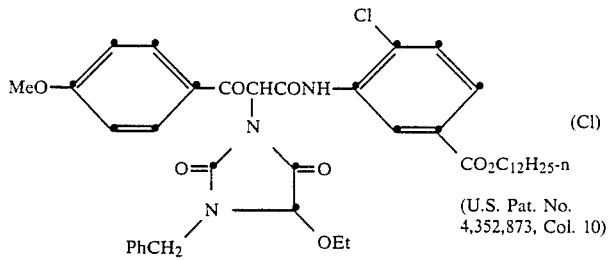

(C1)

(U.S. Pat. No. 4,352,873, Col. 10)

35mm test strips were exposed through a 0-0.3 neutral density (ND) stepwedge test object (0.1 incremental steps) and Daylight V, Wratten 35 and 38A filters and the correct ND filters to give an optical density of ca. 1.0. The strips were processed through a deep-tank sink line at 37.8° C. using the following standard process:

| Color Developer     | 2.5 minutes |
| Bleach (FeIII/EDTA) | 4.0 minutes |
| Wash                | 2.0 minutes |
| Fix                 | 4.0 minutes |
| Wash                | 2.0 minutes |

The processed strips were then dried to give stepped yellow dye images. C-41 processing chemicals were used with 4-amino-3-methyl-N-ethyl-N-2-hydroxyethyl-aniline sulphate as the active component of the color developer solution. Samples for fading were cut from the yellow dye image step with density closest to 1.0. Visible absorption spectra (normalized to 1.0 density) were obtained using a Pye Unicam SP-100 Spectrometer. The dye sample patches were tested for light stability using the EDIE fadeometer for a fade time of 200 hours. The spectrometric curves are remeasured after the fade period and the degree of fade quoted as the fractional decrease in density at the absorption maximum ($\Delta D$) relative to the initial density (1.0) prior to fading. This figure was then divided by the $\Delta D$ of the internal reference coupler C1 to give $$\frac{\Delta D(TC)}{\Delta D(C1)}$$

wherein TC = test coupler. Thus all the data quoted will be relative to a common reference position.

The method used in the EDIE fadeometer is as follows: the dye samples (protected by a Wratten 2B filter) are carried on a fixed plate on both sides of which are set a pair of 'Osram' Colour Matching Fluorescent tubes (75–85 Watt, a total luminous flux level of 18.8 klux), 2 cm apart and 4 cm from the plate in a humidity controlled room at 20° C., 50% RH. The fluorescent tubes emit mainly in the range 400–700nm.

The results are given below in Table VI together with the results for comparative couplers. All couplers are as identified above. It can be seen that the dyes derived from the couplers of the present invention exhibit superior light stability over their prior art counterparts.

TABLE VI

| Coupler | ΔD(TC) ΔD(Cl) 200 h EDIE |
|---|---|
| A3 | 1.6 |
| A2 | 1.8 |
| B2 | 3.9 |
| A5 | 1.5 |
| B5 | 2.0 |
| A8 | 1.9 |
| B8 | 2.5 |
| A9 | 1.6 |
| B9 | 2.3 |
| A10 | 1.7 |
| B10 | 3.6 |
| A11 | 1.8 |
| B11 | 2.8 |
| A12 | 2.1 |
| B12 | 3.7 |
| A13 | 1.4 |
| B13 | 2.6 |
| A15 | 1.5 |
| B15 | 3.0 |
| B16 | 3.3 |
| B10 | 3.6 |
| B17 | 2.0 |
| B2 | 3.9 |

EXAMPLE 3

Coupler Crystallinity in Coatings

Coatings made by the method of Example 2 were assessed on a scale of 0–10 (0=totally clear, 10=totally crystalline) by eye. The results are shown in Table VI.

TABLE VII

| Coupler | Crystallinity rating |
|---|---|
| A6 | 0 |
| B6 | 3 |
| A13 | 0 |
| B13 | 3 |
| A14 | 0 |
| B14 | 10 |
| A15 | 0 |
| B15 | 8 |
| B16 | 3 |

As described, formation of a dye according to the invention is carried out by reacting a benzoylacetanilide coupler, also as described, with the oxidized form (DOX) of a color developing agent, such as a paraphenylenediamine color developing agent. Examples of useful paraphenylenediamine color developing agents are represented by the formula:

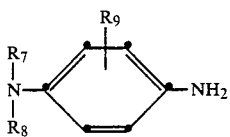

wherein
$R_7$ and $R_8$ are individually unsubstituted or substituted alkyl, such as methyl, ethyl, propyl and butyl; and $R_9$ is hydrogen or one or more substituents, such as alkyl, alkoxy, or alkyl substituted with such groups as carboxy, sulfonic acid, alkanesulfonamido and hydroxy. They are commonly available in the form of salts such as hydrochlorides or sulfates.

The invention has been described in detail with particular reference to preferred embodiments thereof, but it will be understood that variations and modifications can be effected within the spirit and scope of the invention.

What is claimed is:

1. A photographic element comprising a support bearing at least one photographic silver halide emulsion layer and having associated therewith at least one nondiffusible, yellow dye image-forming benzoylacetanilide coupler having an aryloxy coupling-off group wherein (a) the benzene ring of the benzoyl group of the coupler comprises a substituent $R^1O-$ wherein $R^1$ is an alicyclic, or aliphatic, unsubstituted or substituted, branched or unbranched hydrocarbon group; and, (b) the benzene ring of the acetanilide group comprises a substituent attached directly thereto via a linking group L of the formula $$-O-CO-, -CO-O-, -O-, -S-, -SO_2-,$$

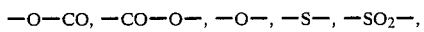

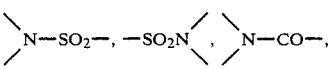

wherein the substituent comprises an unsubstituted branched alkyl group containing at least 4 carbon atoms.

2. A photographic element as in claim 1 wherein the benzoylacetanilide coupler is represented by the formula:

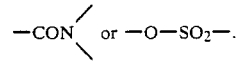

wherein
$R^1$ is an unsubstituted or substituted, branched or unbranched alicyclic or aliphatic hydrocarbon group;
$R^2$ is an unsubstituted or substituted aryl group; and wherein the ring B comprises a substituent attached directly thereto via said linking group L wherein the substituent comprises an unsubstituted branched alkyl group containing at least 4 carbon atoms.

3. A photographic element as in claim 1 wherein the branched alkyl group contains a chiral carbon atom.

4. A photographic element as in claim 1 wherein the branched alkyl group is represented by the formula:

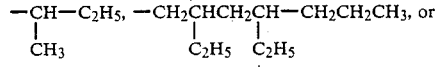

-continued

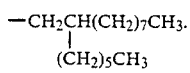

5. A photographic element as in claim 1 wherein the aryloxy coupling-off group is:

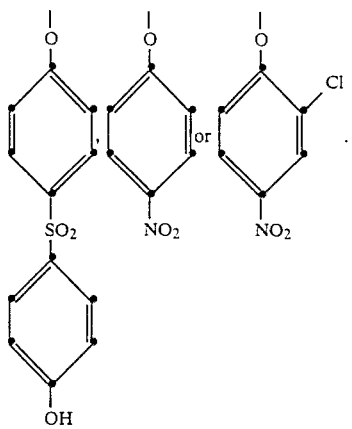

6. A multicolor photographic element comprising a support bearing a yellow dye image-forming unit comprised of at least one blue-sensitive silver halide emulsion layer having associated therewith at least one yellow dye image-forming coupler as defined in claim 1; a magenta dye image-forming unit comprising at least one green-sensitive silver halide emulsion layer having associated therewith at least one magenta dye image-forming coupler; and a cyan dye image-forming unit comprising at least one red-sensitive silver halide emulsion layer having associated therewith at least one cyan dye image-forming coupler.

7. A process of developing an image in a photographic element comprising a support and a silver halide emulsion containing an imagewise distribution of developable silver halide grains, the process comprising the step of developing the element with a silver halide color developing agent in the presence of at least one non-diffusible, yellow dye image-forming benzoylacetanilide coupler as defined in claim 2.

8. A process as in claim 7 wherein the benzoylacetanilide coupler is as defined in claim 2.

9. A color photographic element comprising a support bearing at least one photographic silver halide emulsion layer and having associated therewith at least one non-diffusible, yellow dye image-forming benzoylacetanilide coupler having an aryloxy coupling-off group wherein the coupler is represented by the formula:

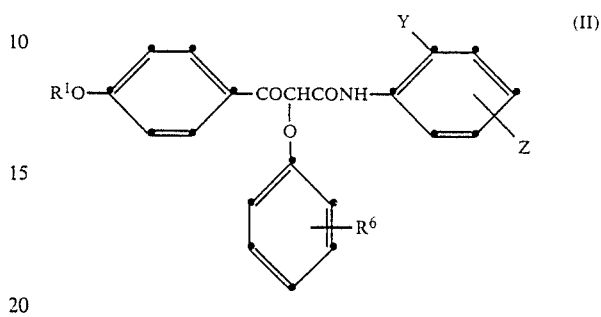

wherein $R^1$ is an unsubstituted branched alkyl group containing at least 4 carbon atoms;

Y is chloro or trifluoromethyl;

Z is $-L^1-R^5$, $-SO_2NR^3R^4$, halogen or trifluoromethyl;

wherein $R^5$ is an unsubstituted or substituted, branched or unbranched aliphatic hydrocarbon group;

$R^3$ and $R^4$ are individually hydrogen or unsubstituted or substituted, branched or unbranched hydrocarbon groups or $R^3$ and $R^4$ together represent the atoms completing a heterocyclic ring;

$R^6$ is at least one of the substituents selected from the group consisting of alkyl, amide, carbamoyl, ester, ketone, sulfonamide, sulfamoyl, sulphone, ether, thioether, nitrile and nitro groups and halogen atoms;

$L^1$ is a direct bond or a carbamoyl, amido, oxycarbonyl, carbonyloxy, sulfonate, ether, sulfamoyl, sulfonamide, phosphate or alkylene group; and, wherein the coupler contains at least one ballast group of sufficient size and configuration to render the coupler non-diffusible in the photographic element.

10. A color photographic element comprising a support bearing at least one photographic silver halide emulsion layer and having associated therewith at least one non-diffusible, yellow dye image-forming benzoylacetanilide coupler having an aryloxy coupling-off group wherein the coupler is selected from the group consisting of:

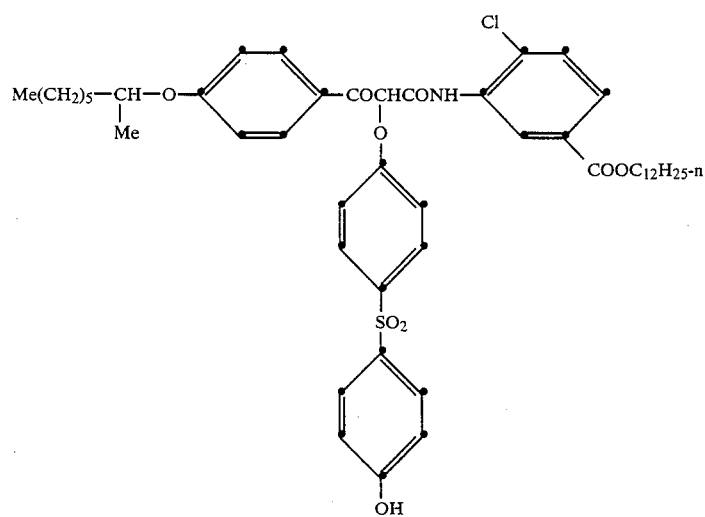
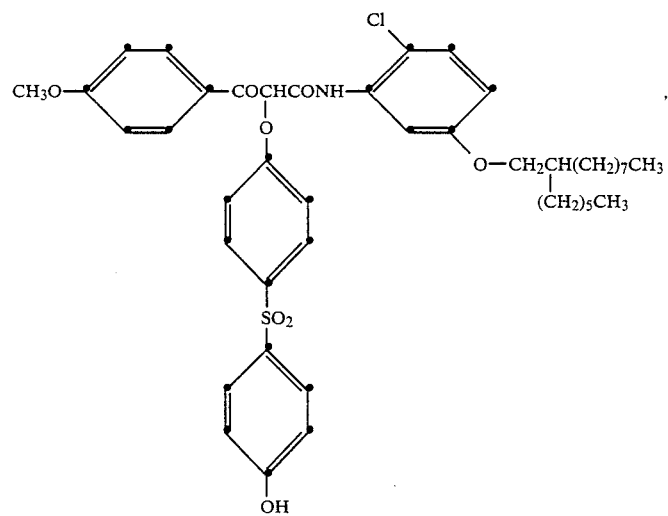
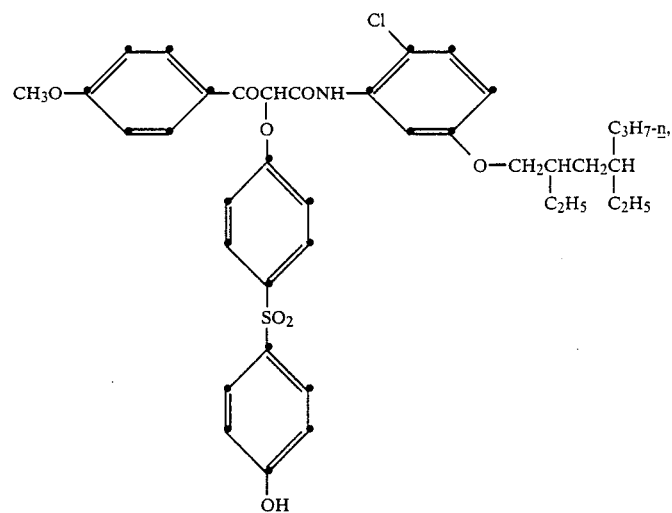

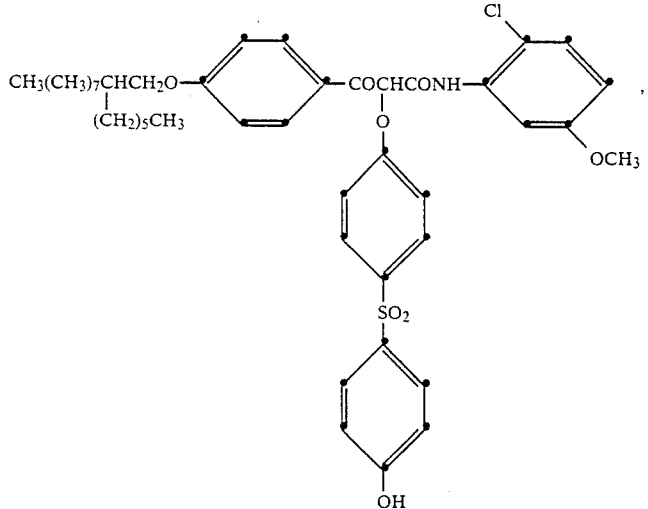

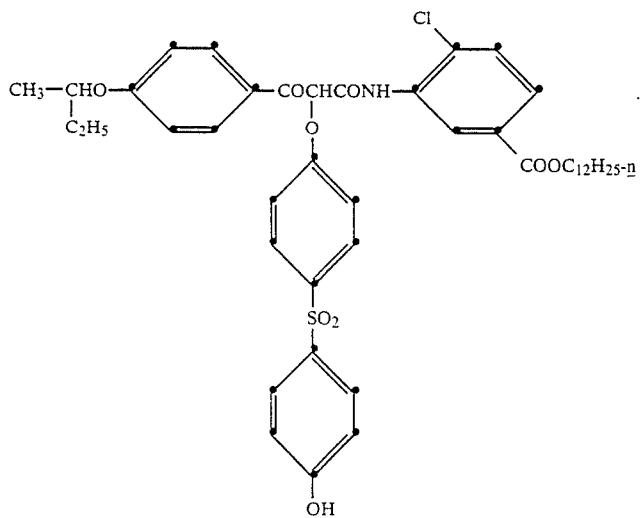

11. A process of developing an image in a photographic element comprising a support and a silver halide emulsion containing an imagewise distribution of developable silver halide grains, the process comprising the step of developing the element with a silver halide color developing agent in the presence of at least one non-diffusible, yellow dye image-forming benzoylacetanilide coupler which is selected from the group consisting of:

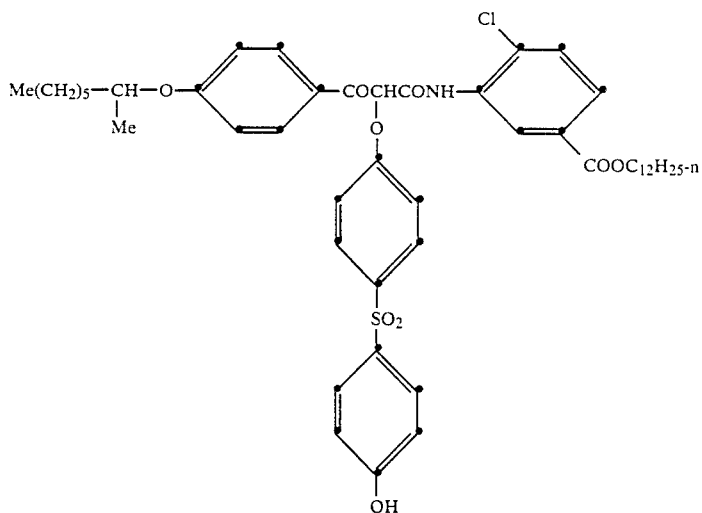

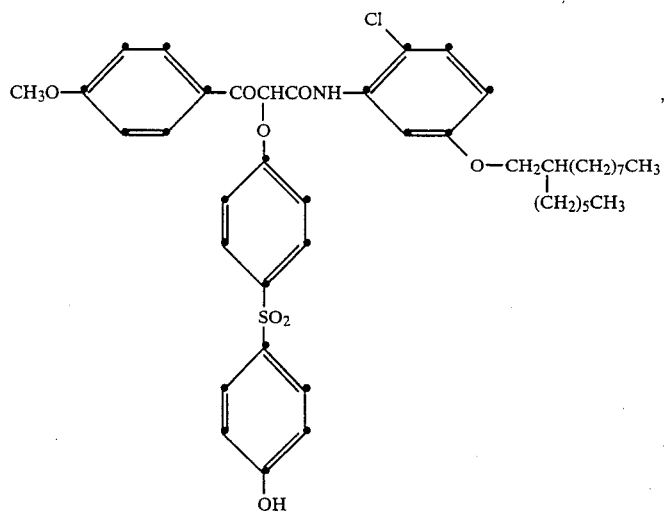
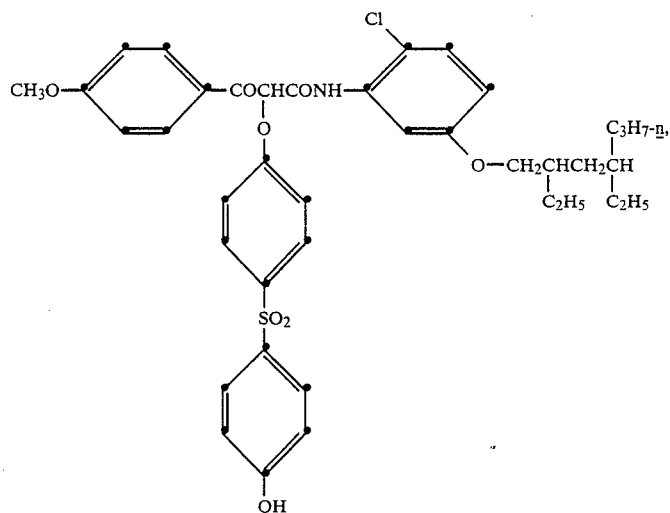
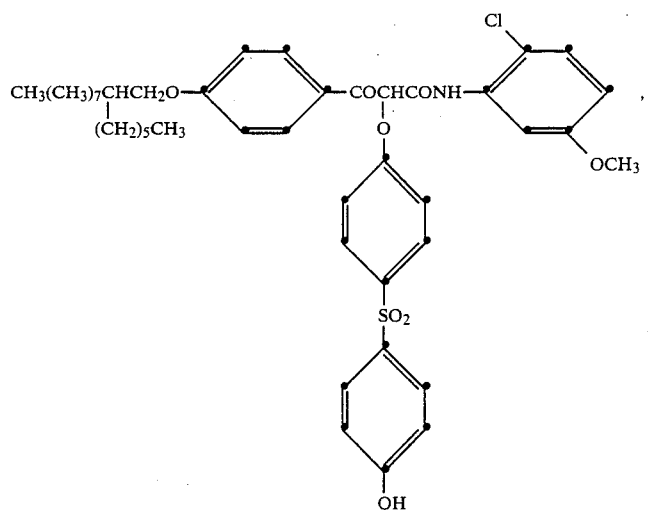

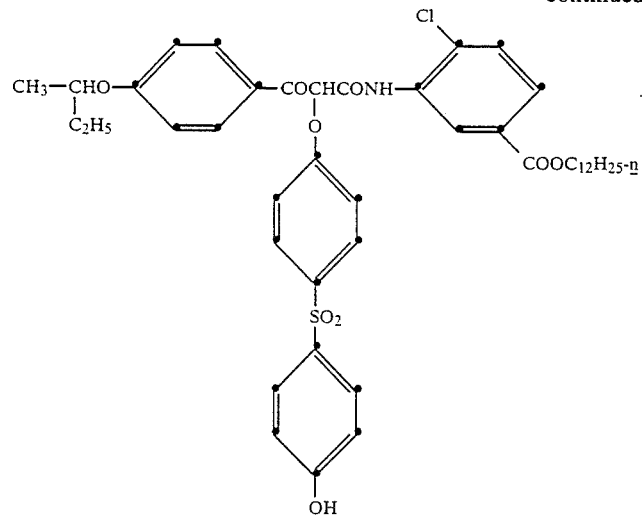

UNITED STATES PATENT AND TRADEMARK OFFICE
CERTIFICATE OF CORRECTION

PATENT NO. : 4,978,605
DATED : December 18, 1990
INVENTOR(S) : Siu C. Tsoi

It is certified that error appears in the above-identified patent and that said Letters Patent is hereby corrected as shown below:

On the title page:

Item [56] References Cited:

"Tsada" should read --Tsuda--.

Column 4, line 25, "oF" should read --of--.
Column 8, line 46, "(1.5l)" should read --(1.5 $\ell$)--.
        line 48, "(1l)" should read --(1$\ell$)--.
        line 53, that part of formula
           reading "oxopropanamidon" should read --oxopropanammido--.

Column 8, line 63, "$C_{31}H_{42}ClNO_5$: " should begin new line directly under Found.

Column 15, line 60, "2" should read --1--.

Column 19, between the first and second formulas, --or-- should be inserted.

Signed and Sealed this

Tenth Day of August, 1993

Attest:

MICHAEL K. KIRK

Attesting Officer     Acting Commissioner of Patents and Trademarks